US006181764B1

(12) United States Patent
Solomon et al.

(10) Patent No.: US 6,181,764 B1
(45) Date of Patent: Jan. 30, 2001

(54) IMAGE RECONSTRUCTION FOR WIDE DEPTH OF FIELD IMAGES

(75) Inventors: Edward G. Solomon, Menlo Park; Robert E. Melen, Saratoga; Robert E. Alvarez; Daniel J. Rachlin, both of Mountain View, all of CA (US)

(73) Assignee: Cardiac Mariners, Inc., Los Gatos, CA (US)

( * ) Notice: Under 35 U.S.C. 154(b), the term of this patent shall be extended for 0 days.

(21) Appl. No.: 09/167,413

(22) Filed: Oct. 6, 1998

(51) Int. Cl.[7] .................................................. A61B 6/03
(52) U.S. Cl. ................................. 378/4; 15/901
(58) Field of Search ........................ 378/4, 8, 15, 19, 378/62, 901; 382/131

(56) References Cited

U.S. PATENT DOCUMENTS

| | | | |
|---|---|---|---|
| 2,638,554 | 5/1953 | Bartow et al. | 250/99 |
| 3,499,146 | 3/1970 | Richards | 250/61.5 |
| 3,742,236 | 6/1973 | Richards | 250/321 |
| 3,746,872 | 7/1973 | Ashe et al. | 250/313 |
| 3,778,614 | 12/1973 | Hounsfield | 250/362 |
| 3,809,886 | 5/1974 | Cochran et al. | 250/323 |
| 3,818,220 | 6/1974 | Richards | 250/61.5 |
| 3,873,834 | 3/1975 | Dammann et al. | 250/323 |
| 3,944,833 | 3/1976 | Hounsfield | 250/367 |
| 3,973,128 | 8/1976 | LeMay | 250/445 |
| 3,979,594 | 9/1976 | Anger | 250/369 |
| 4,010,370 | 3/1977 | LeMay | 250/366 |
| 4,144,457 | 3/1979 | Albert | 250/445 |
| 4,188,640 | 2/1980 | Dittrich et al. | 358/111 |
| 4,573,179 | 2/1986 | Rutt | 378/10 |
| 4,598,369 | 7/1986 | Wang et al. | 364/414 |
| 4,630,296 | 12/1986 | Haaker et al. | 378/2 |
| 4,674,046 | * 6/1987 | Ozeki et al. | |
| 4,730,350 | 3/1988 | Albert | 378/10 |
| 4,853,540 | 8/1989 | Nakajima | 250/327.2 |
| 4,903,204 | 2/1990 | Dobbins, III | 364/413.24 |
| 5,022,066 | 6/1991 | Haaker et al. | 378/2 |
| 5,259,012 | 11/1993 | Baker et al. | 378/21 |
| 5,467,404 | * 11/1995 | Vuylsteke et al. | |
| 5,644,612 | 7/1997 | Moorman et al. | 378/98.2 |
| 5,699,799 | * 12/1997 | Xu et al. | |
| 5,926,568 | * 7/1999 | Chancy et al. | |

FOREIGN PATENT DOCUMENTS

| | | | |
|---|---|---|---|
| WO 94/23458 | 10/1994 | (WO) | H01L/31/115 |
| WO 96/25024 | 8/1996 | (WO) | H05J/35/00 |

OTHER PUBLICATIONS

Digiray, "Digiray's Reverse Geometry X-ray System", Digiray Marketing Brochure, Dec. 1992.*
Curry et al., *Christensen's Physics of Diagnostic Radiology*, Fourth Edition, Lea & Febiger, 1990, pp. 1–522.
Barrett et al., "The Theory of Image Formation, Detection, and Processing", vol. 2, *Radiological Imaging*, published at least by Dec., 1981, pp. 368–371.
Digiray, "Digiray's Reverse Geometry X-ray System", *Digiray Marketing Brochure*, at least by Dec. 1992, pp. 1–2.
Gray, "Application of Optical Instrumentation in Medicine VII", Proceedings of the Society of Photo–Optical Instrumentation Engineers, Mar. 25–27, 1979, vol. 173, pp. 88–95.

* cited by examiner

*Primary Examiner*—David V. Bruce
(74) *Attorney, Agent, or Firm*—Lyon & Lyon LLP

(57) ABSTRACT

An x-ray imaging system capable of local focussing to any depth is disclosed. According to an aspect, the invention comprises a method of generating a volume of data comprising image information for a plurality of depths with an object under investigation, and selecting data from the volume of data to generate a display image.

38 Claims, 7 Drawing Sheets

IMAGE RECONSTRUCTION FOR WIDE DEPTH OF FIELD IMAGES

BACKGROUND

1. Field of the Invention

The invention pertains to the field of diagnostic x-ray imaging, including among other things, techniques for generating images representative of structures within an object.

2. Description of Related Art

Real-time x-ray imaging is increasingly being required by medical procedures as therapeutic technologies advance. For example, many electro-physiologic cardiac procedures, peripheral vascular procedures, PTCA procedures (percutaneous transluminal catheter angioplasty), urological procedures, and orthopedic procedures require the use of real-time x-ray imaging. In addition, modem medical procedures often require the use of instruments, such as catheters, that are inserted into the human body. These medical procedures often require the ability to discern accurately locations of instruments that are inserted within the human body, often in conjunction with an accurate image of the surrounding body through the use of x-ray imaging.

A number of real-time x-ray imaging systems are known. These include fluoroscope-based systems where x-rays are projected into an object to be imaged, and shadows caused by relatively x-ray opaque matter within the object are displayed on a fluoroscope located on the opposite side of the object from the x-ray source. However, such systems have great difficulty forming images that distinguish particular structures or regions within the depth of the object to be imaged (i.e., where the image is "focused" upon particular structures or regions of interest within the object). This is due in part to the geometry of such fluoroscope-based systems, in which the x-ray opaque properties of the entire depth of the object contributes to the final image, regardless of the exact depth of specific x-ray opaque structures/regions within the object.

One approach to generating an image of particular structures or regions within an object is provided by computed tomography ("CT") imaging systems. In operation, CT systems perform multiple x-ray projections or x-ray measurements of the object to be imaged from multiple angles. The data from the multiple projections can be manipulated to construct an image of a particular plane/slice within the object. Multiple image planes/slices can be made at various depths within the object by moving the CT imaging system and the object relative to each other. However, conventional CT systems are not able to generate a focussed image of a particular structure within an object if the structure of interest lies across multiple image planes/slices at various depths within the object.

Another approach to x-ray imaging involves the use of reverse-geometry x-ray imaging systems. In such systems, an x-ray tube is employed in which an electron beam is generated and focussed upon a small spot on a relatively large target assembly, emitting x-ray radiation from that spot. The electron beam is deflected in a scan pattern over the target assembly. A relatively small x-ray detector is placed at a distance from the target assembly of the x-ray tube. The x-ray detector converts x-rays that strike it into an electrical signal indicative of the amount of x-ray flux detected at the detector. One advantage provided by reverse-geometry systems is that the geometry of such systems allows x-rays to be projected at an object from multiple angles without requiring physical relocation of the x-ray tube. However, the particular x-ray detector used in such systems often limits the spatial resolution of such systems, thereby limiting the quality/range of images that can be obtained. Moreover, known reverse-geometry x-ray imaging systems do not have the functionality to generate a focussed image of structures at various depths within an object.

Therefore, it is desired to create an imaging system that can generate an accurate representation of internal structures within an object.

SUMMARY OF THE INVENTIONS

The present invention comprises an x-ray imaging system capable of local focusing to any depth within an object. According to an aspect, the invention comprises a method of generating a volume of data comprising image information for a plurality of depths with an object under investigation, and selecting data from the volume of data to generate a display image. The criteria for selecting the data to display is based upon characterization of the portions of the object illuminated by the x-ray beam.

In an embodiment, a method of the present invention is directed to generating a charged particle beam with a charged particle beam source within an x-ray source; moving the charged particle beam across a target assembly within the x-ray source; emitting x-rays from the target assembly; passing the x-rays through an object; detecting the x-rays with a plurality of detectors; creating a plurality of image planes/slices from information obtained by the plurality of detectors as a result of detecting the x-rays, each image plane/slice of the plurality of image planes/slices corresponding to an object plane/slice defining a portion of the object; creating an image by selecting data from the plurality of image planes/slices.

These and other objects, aspects, and advantages of the present inventions are taught, depicted and described in the drawings, description, and claims of the invention contained herein.

DESCRIPTION OF THE PREFERRED EMBODIMENTS

Figure 1:
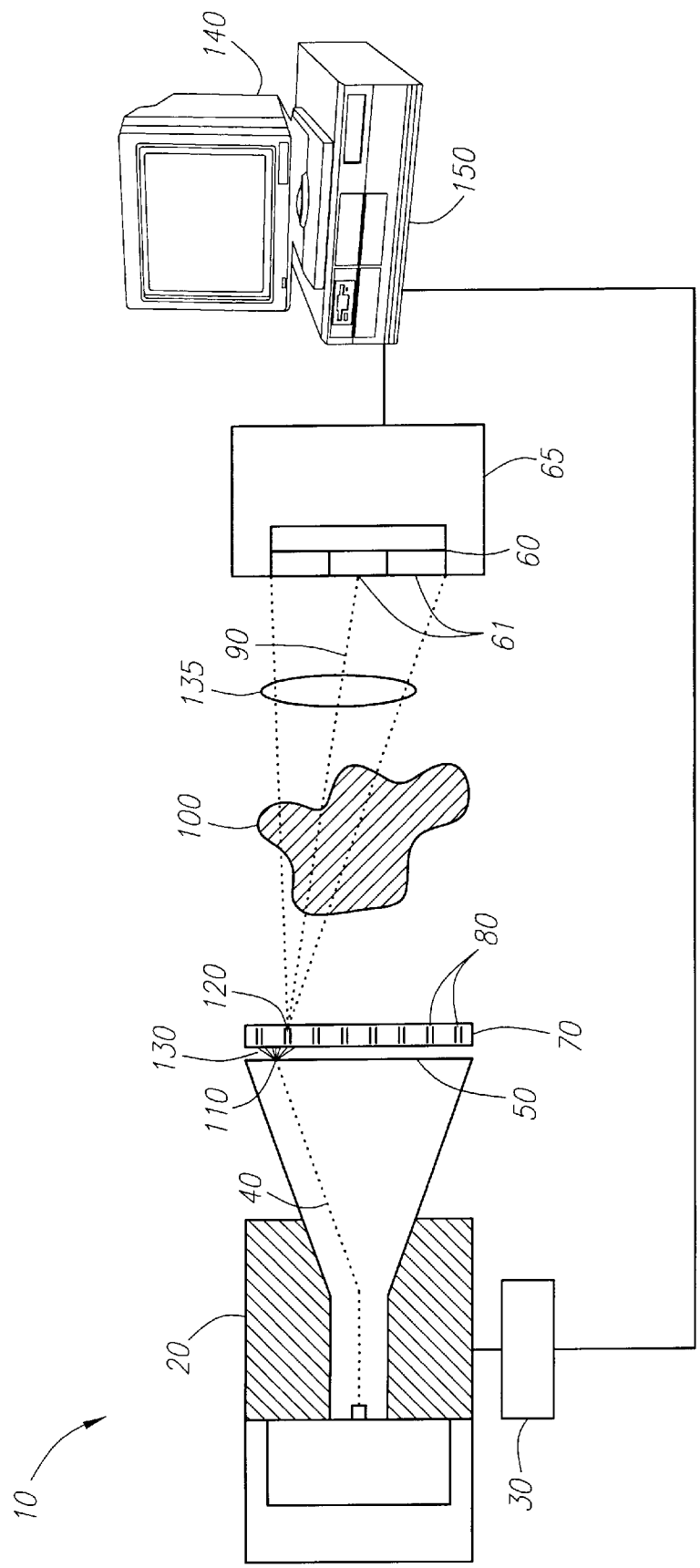
FIG. 1 is a diagram showing components of an x-ray imaging system according to the present inventions.

FIG. 1 is a diagram showing the high level components of an embodiment of a x-ray imaging system according to the invention. X-ray source 10 includes an electron beam source comprising a power supply which can operate x-ray source 10 at about −70 kV to −120 kV. In the present embodiment, this voltage level produces a spectrum of x-rays ranging to 120 keV. Electron beam 40, which is generated within x-ray source 10 by a charged particle gun, is deflected over the surface of a target assembly 50 (which is a grounded anode in an embodiment of the invention) in a predetermined pattern, e.g., a scanning or stepping pattern. X-ray source 10 includes a mechanism to control the movement of electron beam 40 across target assembly 50, such as a deflection yoke 20 under the control of an electron beam pattern generator 30. One advantage provided by the geometry of x-ray source 10 is that it allows x-rays to be projected at an object 100 from multiple angles without requiring physical relocation of the x-ray source 10.

A preferred x-ray source 10 is disclosed in copending U.S. patent application Ser. Nos. 09/167,399 09/167,524 and a preferred target assembly 50 is disclosed in copending U.S. patent application Ser. No. 09/167,523, all filed concurrently with the present application, all of which are incorporated by reference in their entirety. A method and apparatus for generating and moving electron beam 40 across target 50 is disclosed in commonly owned U.S. Pat. No. 5,644,612 which is incorporated herein by reference in its entirety.

In FIG. 1, a collimating assembly is located between target assembly 50 of x-ray source 10 and a multi-detector array 60. In the preferred embodiment, the collimating assembly is located between target assembly 50 and the object 100 for which an image is to be obtained. The presently preferred collimating assembly is collimator grid 70, containing a plurality of x-ray transmissive apertures 80 arranged in a grid pattern. Collimator grid 70 is designed to permit passage of x-rays forming a diverging beam 135 that directly intercepts multi-detector array 60. In an embodiment, collimator grid 70 utilizes a cooling assembly and beam hardening filters. Examples of preferred collimator grids and beam hardening filters that can be utilized in the invention include these depicted and disclosed in copending U.S. Pat. No. 5,859,893, and U.S. patent application Ser. No. 09/167,639 filed concurrently with the present application, both of which are hereby incorporated by reference in their entirety.

In operation, electron beam 40 preferably dwells at location 110 on target assembly 50 which is located substantially at a position where the axis 90 for a particular aperture 120 of collimator grid 70 intersects the target assembly 50. As the electron beam 40 strikes target assembly 50 at location 110, a cascade of x-rays 130 is emitted. Only the portion of the cascade of x-rays 130 whose path lies substantially along axis 90 pass through aperture 120 and form a diverging x-ray beam 135. The shape of x-ray beam 135 is influenced by the shape of aperture 120. For instance, if the aperture is square the x-ray beam 135 takes on a generally truncated pyramidal shape. If the aperture is circular, x-ray beam 135 takes on a generally conical shape. In a preferred embodiment, the shape and area of the aperture is such that the area of maximum divergence of the x-ray beam 135 is substantially the same as the dimensions of the x-ray capture surface for multi-detector array 60.

Multi-detector array 60 comprises a plurality of discrete detectors (referred to herein as "detector elements") 61 arranged in an array. Each detector element 61 includes a x-ray surface having a capture area for detecting x-rays. Each detector element is capable of independently measuring the amount of x-rays that strike it. When an object 100 is interposed between the x-ray source 10 and the multi-detector array 60, some of the x-rays in x-ray beam 135 will pass through a portion of object 100, and if not scattered or absorbed, will strike the detector elements that make up multi-detector array 60. The x-rays that strike any individual detector element comprise a portion of x-ray beam 135 that is referred to herein as an x-ray beam subpath.

In a preferred embodiment, each detector element comprises components for measuring the quantity of x-ray photons that strike the detector element and outputting a signal representative of that measurement. Alternatively, each detector element includes components for generating an electrical signal generally proportional to the total energy of the x-rays that strike the detector element. The magnitude of the generated electrical signals corresponds to the flux intensity of the x-rays from the appropriate x-ray beam subpath of x-ray beam 135. Utilizing a multi-detector array 60 that independently measures the x-rays which strike each detector element results in the generation of x-ray transmissiveness information that is proportional to the x-ray flux passing through object 100 along particular x-ray beam subpaths. The resulting intensity data can be used or manipulated to create a representation of object 100, i.e. a representation of the x-ray transmissiveness of object 100, which can be displayed on monitor 140. The presently preferred detector array is disclosed and described in corresponding U.S. application Ser. No. 09/167,397 and U.S. application Ser. No. 09/167,318 filed concurrently herewith, both of which are incorporated by reference in their entirety.

In one embodiment, the number of apertures 80 in collimator grid 70 corresponds to the number of image pixels that are to be displayed on monitor 140 or other visual display devices that can be connected to the video output of the x-ray imaging system. Alternatively, the image pixel to aperture ratio is increased, so that the number of apertures are less than the number of image pixels that are displayed on a display device. An "object pixel," for purposes of this discussion, is an area in a plane of the object about which information is being collected. An image pixel is a picture element that is an image representation of one or more object pixels. The presently preferred number of apertures is 10,000 arranged in a 100 by 100 grid. The number of apertures suggested above is for illustrative purpose only and depends on the particular application to which the invention is directed.

X-ray transmissiveness information obtained from the detector elements 61 pertinent to specific image pixels are reconstructed by image reconstruction system 65, as will be described in further detail below. In an embodiment, image reconstruction system 65 also performs control functions and display preparation for the x-ray imaging system. Operational instructions and control of the x-ray source 10, detector 60 and image reconstruction system 65 are made through a control workstation 150. Control workstation 150 also receives operational and status information from the various components of the x-ray imaging system.

Figure 7:
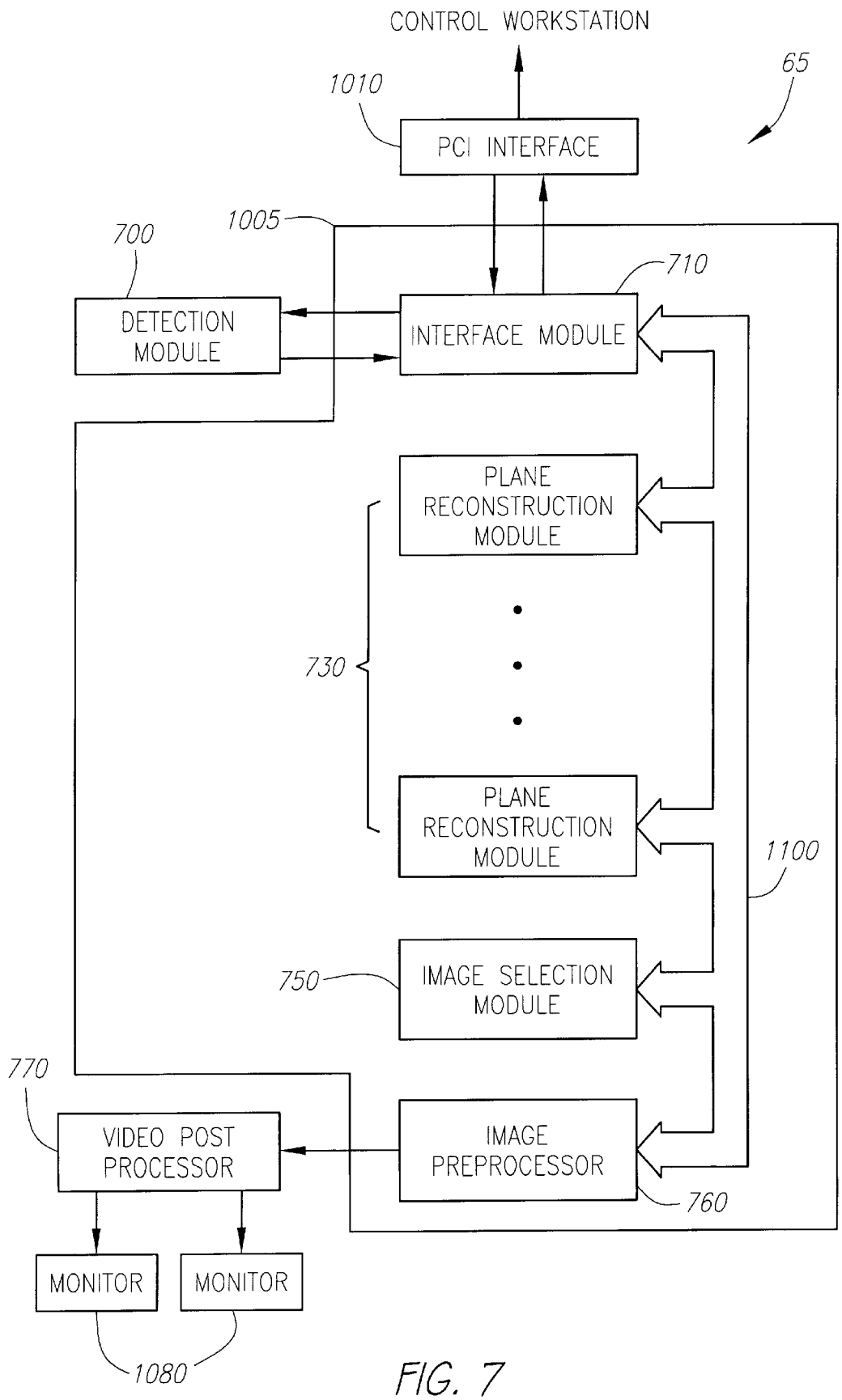
FIG. 7 is a block diagram of a presently preferred image reconstruction system according to the present inventions.

FIG. 7 depicts a block diagram of an embodiment of a preferred image reconstruction system 65. The image reconstruction system 65 comprises a PCI interface 1010, which connects to a control workstation 150. In an embodiment, a detection module 700 comprises the components of multi-detector array 60 and receives x-ray transmissiveness information. Alternatively, multi-detector array 60 is physically separate from the image reconstruction system 65 and the detection module 700 comprises components to receive data signals from the multi-detector array 60. Image reconstruction chassis 1005 comprises an interface module 710, one or more plane reconstruction modules 730, an image selection module 750 and an image preprocessor 760. The various components on the image reconstruction chassis 1005 are interconnected via one or more busses 1100, which also include control lines. PCI interface 1010 and detection module 700 are coupled to interface module 710, whereas image preprocessor 760 is coupled to video post processor 770. Video post processor 770 is coupled to display monitors 1080. Details of the components depicted with reference to FIG. 7 are described in more detail in copending U.S. patent application Ser. No. 09/167,171, filed on even date herewith, which is incorporated herein by reference in its entirety.

For certain applications it may be desirable or necessary to utilize more x-ray flux for each area of object 100 than can be obtained from a single emission from a single aperture. This may occur, for example, if the target assembly material is unable to withstand sufficient electron beam bombardment at one emission (e.g., because of heat generated by the bombardment) necessary to generate the desired amount of x-ray flux. In these applications, multiple smaller x-ray emissions from a single aperture can be performed. The additional x-ray flux can create a potentially more accurate image by decreasing quantum noise. The preferred methods and patterns of stepping electron beam 40 across target assembly 50 is described more fully in copending patent application Ser. No. 09/167,405 filed concurrently with this patent application, which is incorporated herein by reference in its entirety.

In many reverse-geometry x-ray systems, the spatial resolution of the resulting image is in large part determined by the capture area of a single detector. Generally speaking, a non-segmented detector with a small capture area can provide high spatial resolution and poor collection efficiency (i.e., the ratio of the meaningful photons passing through the object to the total number of photons passing through the object), while a non-segmented detector with a large capture area provides high collection efficiency and poor spatial resolution. To address this problem, the present invention utilizes a multi-detector array having a relatively large capture area that comprises a plurality of individual detectors with each detector having a relatively small capture area.

Figure 2:
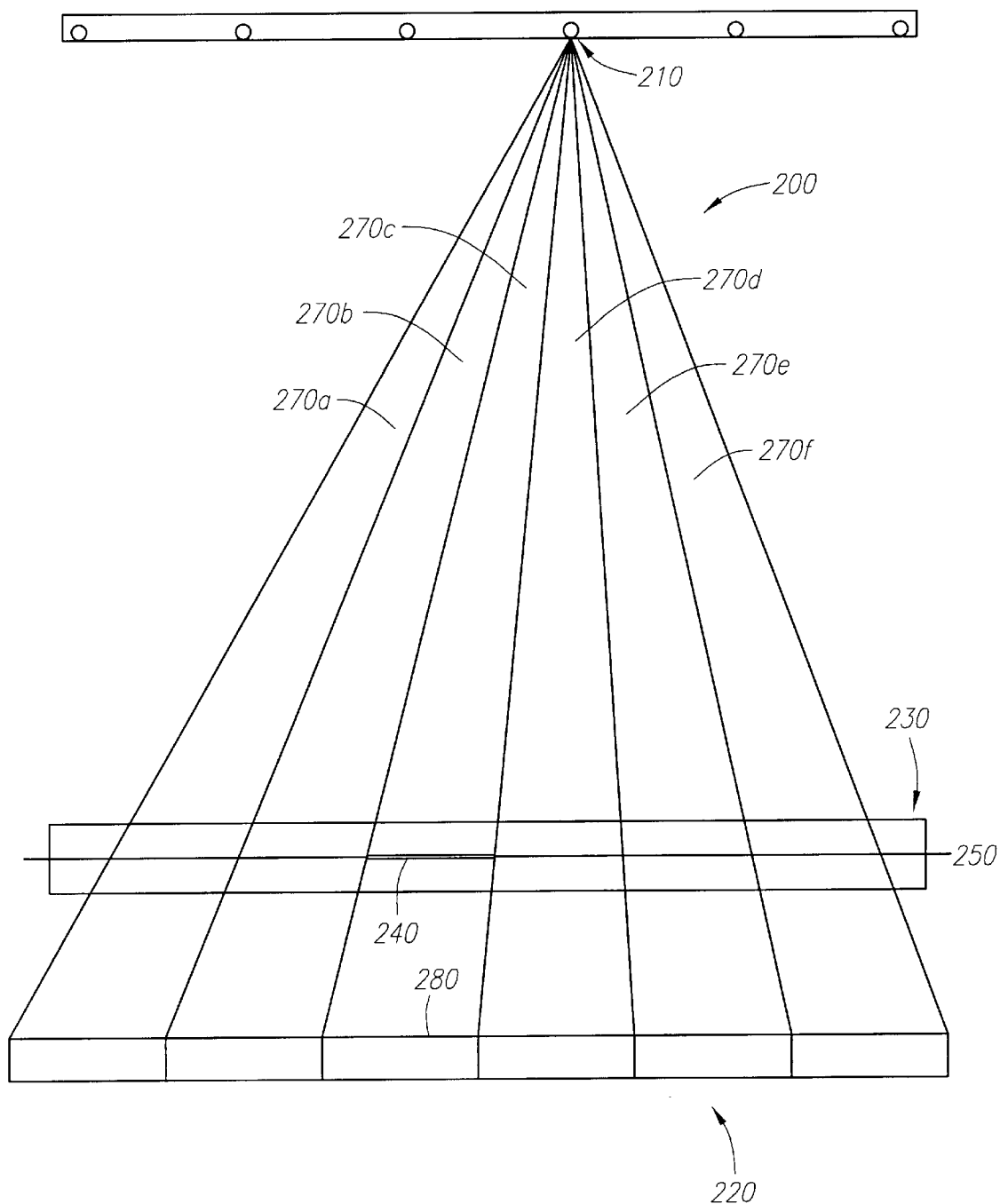
FIG. 2 depicts an x-ray path emanating from a single aperture in a collimator grid and passing through an object on its way to a detector array.

Referring to FIG. 2, a diverging x-ray beam path 200 is depicted emanating from an aperture 210 of a collimator grid and extending to a multi-detector array 220. The x-ray beam path 200 passes through an object 230 on its way to the multidetector array 220. The x-ray beam path 200 intersects object 230 at various planes of interest, such as object plane 250.

X-rays traveling along x-ray beam path 200 diverge after exiting aperture 210, preferably having a cross sectional area varying from a minimum area approximately equal to the size of the aperture up to a maximum area approximately equal to an area covering the detection surface of multi-detector array 220. In an embodiment, multi-detector array 220 is positioned such that the maximum surface area of x-ray beam path 200 only covers the total capture area of the multi-detector array 220 without extending beyond this area. This minimizes the generation of x-rays that provide no meaningful image information.

X-ray beam subpaths 270a, 270b, 270c, 270d, 270e, and 270f are defined by the capture size and quantity of the various detector elements that comprise multi-detector array 220. The shape of the volume of the x-ray beam subpath is essentially defined by the shape of the detector elements. In other words an x-ray beam subpath (e.g., x-ray beam subpath 270c) is the volume defined by the elongated shape having a truncated apex at an aperture 210 and a base having an area of the capture area of a detector element 280. If the detector element capture area is round, the shape of an x-ray beam subpath is substantially conical. If the detector element capture-area is square, the shape of an x-ray beam subpath is substantially pyramidal.

Object pixel 240 is an area within plane of interest 250. When a reconstructed image is displayed, object pixel 240 could be represented by a particular image pixel which is constructed using information obtained from certain x-ray beam subpaths that intersect object pixel 240.

Each detector element 280 of multi-detector array 220 detects x-rays that have passed through object 230 for a particular portion of x-ray beam path 200. The quantity of x-rays detected at a detector element 280 provides information about the x-ray transmissiveness for object 230 at a particular object pixel 240. The x-ray beam path 200 from each aperture 210 provides information to create a group of discrete pieces of information concerning the x-ray transmissiveness of the object. The number of discrete pieces of information generated for x-ray beams emanating from a single aperture corresponds to the number of individual detector elements 280 in the multi-detector array 220. The presently preferred detector array is comprised of 48 by 48 detector elements. Thus, for each x-ray beam 200 emanating from an aperture 210, this results in 2,304 discrete pieces of information concerning the x-ray transmissiveness of object pixels for an object plane defined within the object. The x-ray transmissiveness information obtained by the detector elements from each of the x-ray beam subpaths is available for use in generating image pixel information.

Figure 3:
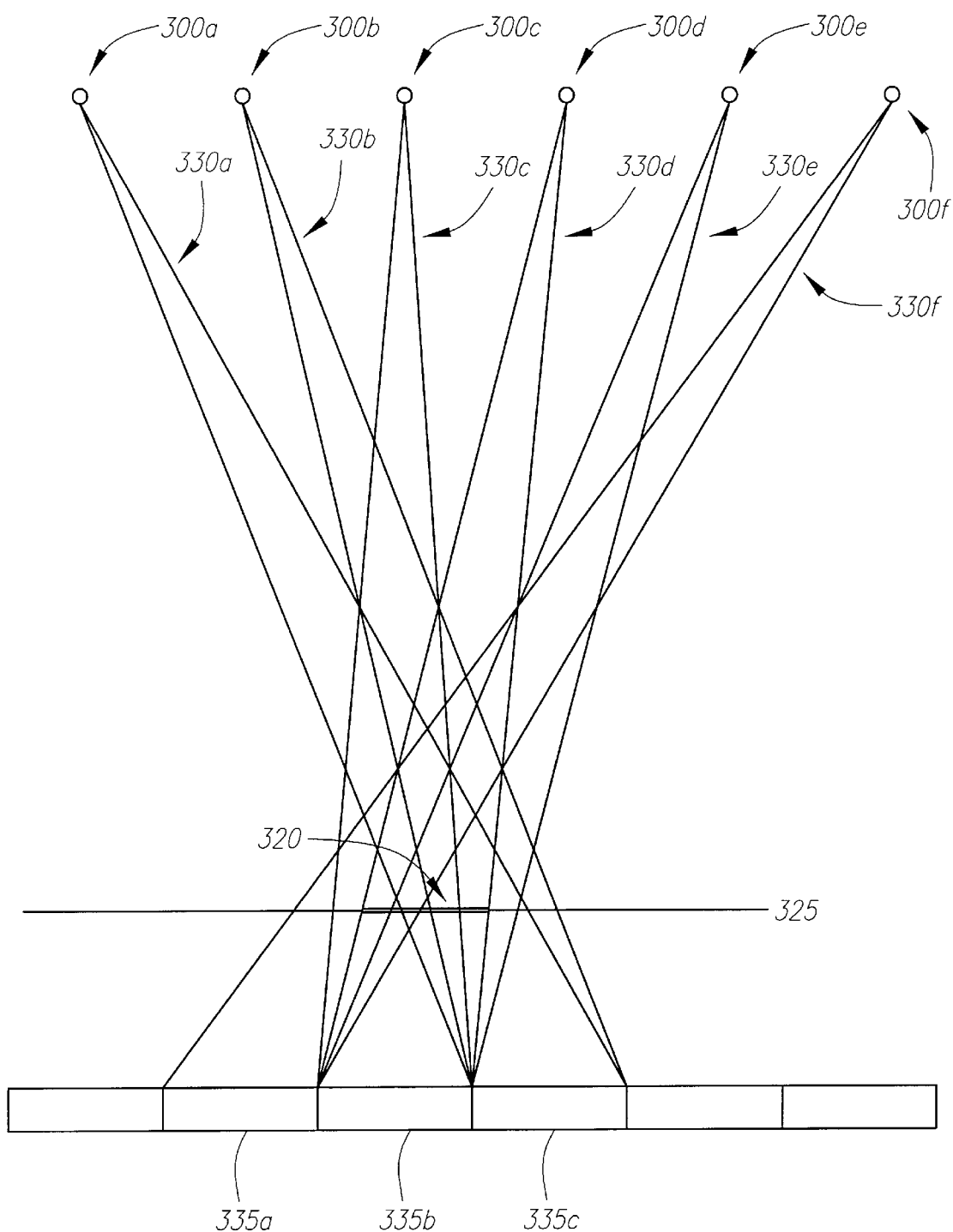
FIG. 3 depicts multiple x-ray beam subpaths emanating from multiple apertures in a collimator grid and passing through an object to a detector array.

Imaging data for object pixels can be generated by collecting x-ray transmissiveness information measured for x-ray beam subpaths that intersect a particular object pixel on a particular plane of interest. Depending on the plane of interest chosen, the intersection of the subpaths on that plane of interest may not be fully coincident but may be only partially coincident. Referring to FIG. 3, shown are x-ray beam subpaths 330a, 330b, 330c, 330d, 330e, and 330f emanating from apertures 300a, 300b, 300c, 300d, 300e and 300f respectively. Each of these x-ray beam subpaths are portions of their respective x-ray beams that are either completely or partially coincident with object pixel 320 on a plane of interest 325. By taking into consideration the x-ray transmissiveness information obtained by the detectors 335a–c for x-ray beam subpaths 330a–f (along with any other x-ray beam subpath-detector combinations that provide relevant information about object pixel 320), image data that accurately represents the x-ray transmissiveness of an object at object pixel 320 can be reconstructed.

Figure 4:
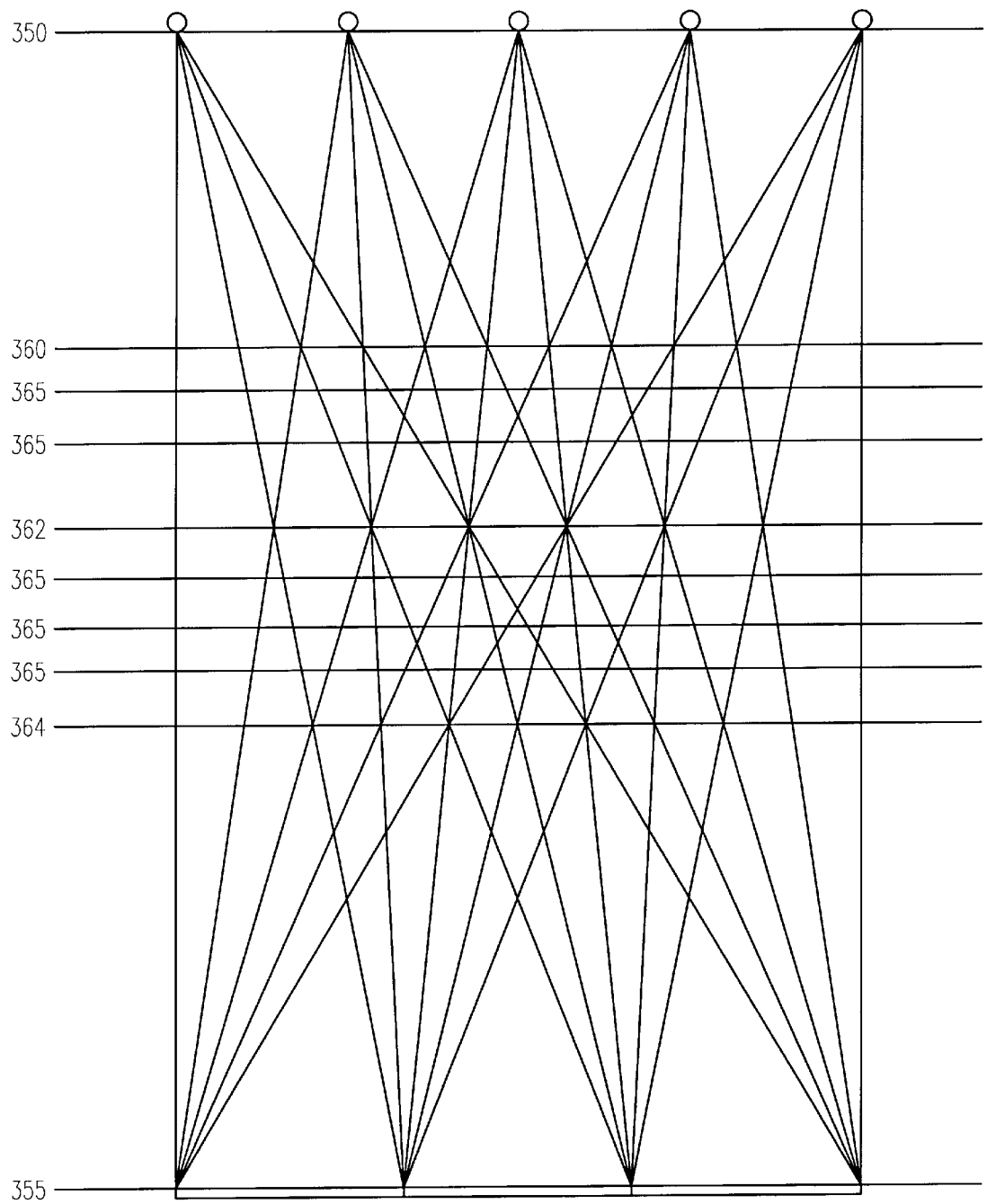
FIG. 4 is a diagram that shows the location of a plurality of planes between a source plane and a detector plane according to one embodiment of the present inventions.

As depicted in FIG. 4, there are numerous planes parallel to the source plane 350 and detector plane 355. Some of the parallel planes are located where multiple x-ray beam subpaths are fully coincident through regularly-spaced areas in the plane. These planes are referred to as focal planes and the regularly spaced areas within the plane can be identified as object pixels. Examples of focal planes in FIG. 4 are planes 360, 362, and 364. Each focal plane comprises characteristics which differ from other focal planes, including distance from the source, pitch of the object pixels, and specific areas of the object that intersects the focal plane. Non-focal planes 365 are located between any two focal planes, and in these non-focal planes, x-ray beam subpaths emanating from the source plane are only partially coincident with each other.

Figure 5:
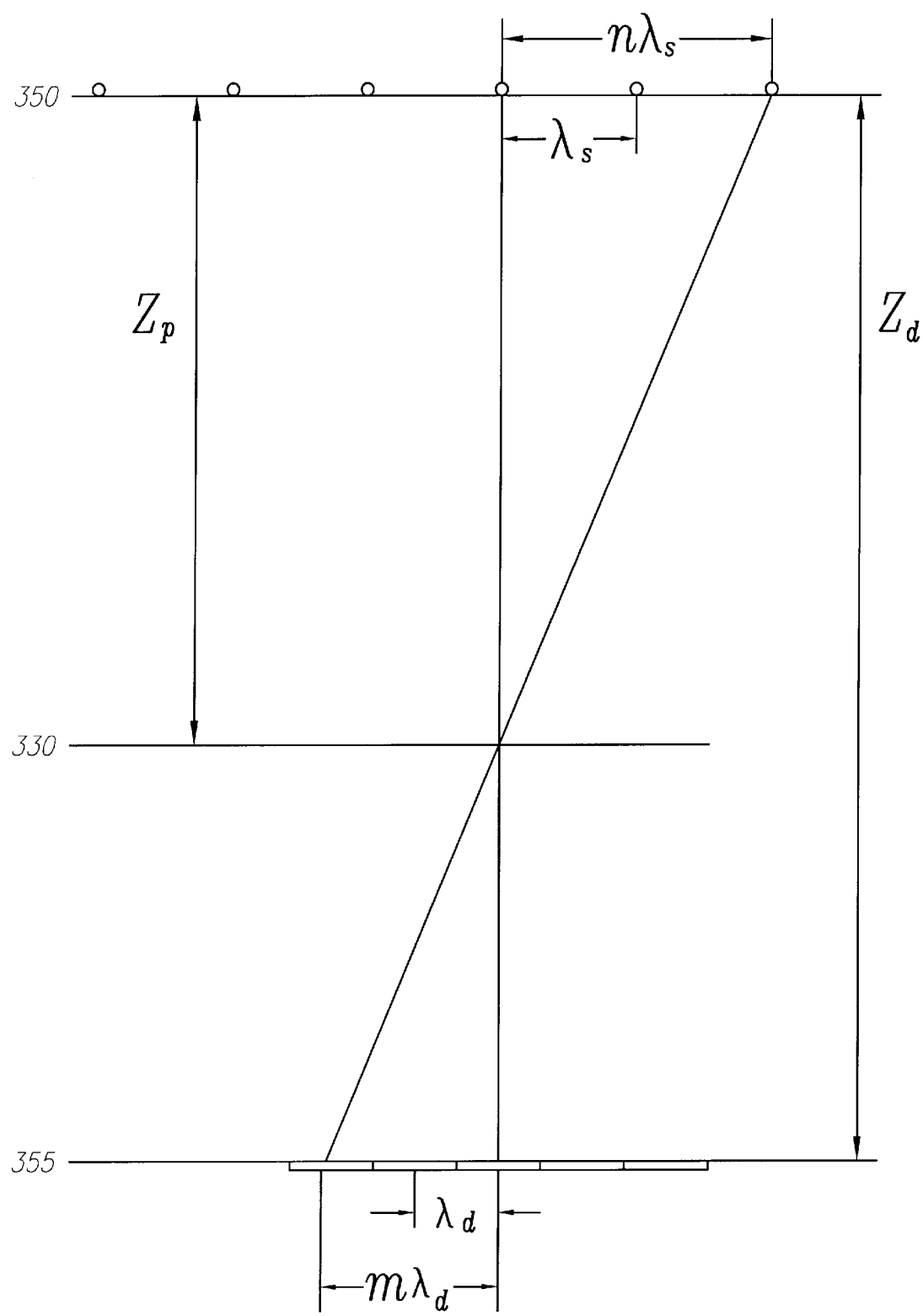
FIG. 5 is a diagram of representative x-ray beam subpaths emanating from regularly-spaced x-ray sources traveling to an array of detectors.

Referring to FIG. 5, a method is provided to reconstruct both focal and non-focal planes as two-dimensional planes of object pixels. Consistent with the invention, an array of x-ray beam source locations, preferably a rectangular array of $SOURCE_x$ by $SOURCE_y$ sources with a pitch $\lambda_s$ in both the x- and y-directions, is used with an array of detectors, preferably a square array of $DET_x$ by $DET_y$ detectors on a pitch $\lambda_d$ in both the x- and y-directions. In an embodiment, each source is a separate aperture within a collimation grid that emanates an x-ray beam path that covers the capture surface of the multi-detector array. Each x-ray beam path is divided into a plurality of x-ray beam subpaths, with the x-rays in each x-ray beam subpath providing intensity data to a single detector element. Thus, there are $DET_x*DET_y$ x-ray beam subpaths per x-ray path and $SOURCE_x*SOURCE_y$ x-ray beam paths for a total of $DET_x*DET_y*SOURCE_x*SOURCE_y$ x-ray beam subpaths from all sources in the array of sources. INTENSITY(i,j,k,l) represents the intensity data for x-rays detected at a detector DET(i,j) from x-rays generated by a SOURCE(k,l).

A focal plane can be described by a pair of natural numbers (integer >1) m and n where $m*\lambda_d$ and $n*\lambda_s$ are the baseline lengths of similar triangles. However, any plane whether focal or non-focal can be reconstructed by use of the present invention. All that is required in order to reconstruct a plane is that the plane being reconstructed be capable of being described by values of m and n which are real numbers greater than zero.

$Z_d$ represents the distance from the source plane 350 to the detector plane 355 while $Z_p$ represents the distance from the source plane 350 to a particular object plane 330. Therefore, the distance $Z_p$ is described by the values of m,n and can be expressed as:

$$Z_p(m, n) = Z_d \frac{n*\lambda_s}{n*\lambda_s + m*\lambda_d} \qquad \text{EQ. 1}$$

According to an embodiment of the invention, reconstruction of a two-dimensional array of image pixels IMAGE (m,n) at an object plane defined by m and n can be performed by creating an array of an image pixel values corresponding to object pixels on the plane. The image pixel values are generated by mathematically manipulating each value of INTENSITY (i,j,k,l) that corresponds to a particular object pixel on the object plane. In an embodiment, the values of INTENSITY (i,j,k,l) for each object pixel are summed to generate the image pixels for an object plane. In the present embodiment, each value of INTENSITY (i,j,k,l) is summed into the appropriate image pixel defined by IMAGE (i*n+k*m,j*n+l*m).

In the case of a non-focal plane, any value which is not a whole number is preferably assigned to the appropriate image pixel based upon the conventional rules of rounding to the whole number. For example, in reconstructing the m=10 and n=1.33 plane, an x-ray beam subpath from a source having the x-y indices (1,1) projecting onto a detector element having the x-y indices (1,2) (which is represented as INTENSITY (1,2,1,1)) corresponds to an object pixel at coordinates (1*1.33+1*10,2*1.33+1*10) or (11.3, 12.7). This x-ray beam subpath passes through and contains information regarding object pixels at coordinates (11, 12), (12, 12), (11, 13), and (12, 13). Thus, the x-ray transmissiveness value obtained from INTENSITY (1,2, 1,1) could be assigned to any of the image pixels at coordinates (11,12), (12,12), (11,13) and/or (12,13). It is presently preferred that the normal rules of rounding apply and object pixel (11.3, 12.7) is assigned to image pixel (11,13). It should be noted that other methods of assigning x-ray beam subpaths to image pixel coordinates can be employed without departing from the scope of the present invention.

The maximum x- and y-indices of array IMAGE (m,n) can be expressed as $DET_x*n+SOURCE_x*m$ and $DET_y*n+SOURCE_y*m$ respectively. In the present embodiment, multiplying the baselines of the similar triangles, e.g., doubling or tripling them, does not change the position of the resulting plane to be imaged.

The pitch $\lambda_p$ of object pixels in a particular object plane $Z_p$ (m,n) can be expressed as follows:

$$\lambda_p(m, n) = \frac{\lambda_d}{n} * \frac{Z_p(m, n)}{Z_d} \qquad \text{EQ. 2(a)}$$

$$= \frac{\lambda_d}{n} * \frac{n*\lambda_s}{n*\lambda_s + m*\lambda_d} \qquad \text{EQ. 2(b)}$$

$$= \frac{\lambda_d*\lambda_s}{n*\lambda_s + m*\lambda_d} \qquad \text{EQ. 2(c)}$$

In an embodiment, every $m^{th}$ detector in the x- and y-directions provides intensity information for use in reconstructing one or more selected object pixels in an object plane. Therefore, there are approximately $DET_x*DET_y/m^2$ detectors or x-ray beam subpaths that provide intensity information per object pixel. Since the total number of x-ray beam subpaths in the present embodiment is $DET_x*DET_y*SOURCE_x*SOURCE_y$, the number of object pixels in an object plane about which x-ray transmissiveness information can be obtained for use in reconstructing an image can be expressed as:

$$\frac{DET_x*DET_y*SOURCE_x*SOURCE_y}{DET_x*DET_y/m^2} = \qquad \text{EQ. 3}$$
$$SOURCE_x*SOURCE_y*m^2$$

Due to the fact that the object pixels around the perimeter of the intersection area do not receive complete intensity information (i.e., the number of detector elements measuring the amount of flux passing through these object pixels are less than for other object pixels), the number of object pixels in an object plane providing meaningful intensity information may be slightly lower than the above number.

For example, the n=1.33 and m=10 plane in a system with a 100×100 array of sources has 1,000,000 (100×100×10²) object pixels in any object plane. Furthermore, the m=10 and n=1.33 plane has 23,040,000 (48×48×100×100) x-ray beam subpaths if a 48×48 array of detector elements is used. In this example, there should be approximately 23 x-ray beam subpaths which are completely or partially coincident to each object pixel. However, due to the geometry of the system, object pixels on the edge of the object plane may have less than 23 x-ray beam subpaths which are completely or partially coincident to them.

When the size of the source array is $SOURCE_x*\lambda_s$ by $SOURCE_y*\lambda_s$, the size of the field of view at a particular object plane can be expressed as:

$$SOURCE_x*\lambda_s*\left(1 - \frac{Z_p}{Z_d}\right) \text{ by } SOURCE_y*\lambda_s*\left(1 - \frac{Z_p}{Z_d}\right) \qquad \text{EQ. 4}$$

The field of view can be changed by using some as opposed to all of the sources of the source array. By using a smaller number of apertures located in a certain area of the collimator grid, the area to be imaged can be made smaller.

In constructing each image plane, the x-ray transmissiveness information should be processed such that it is always associated with the image pixel to which it has been assigned. In addition, if the preferred stepping pattern of the electron beam is utilized, each aperture will emit x-rays more than one time for the creation of a single frame and each detector element will provide x-ray transmissiveness information assigned to the same image pixel more than once. In this situation, it is presently preferred that x-ray transmissiveness information obtained from the same detector element from x-rays emanating from the same aperture in the same frame is combined together prior to combination with other x-ray transmissiveness information assigned to the same image pixels that resulted from x-rays that emanated from other apertures in that frame.

The present invention takes into account that it is not really a two-dimensional plane which is constructed by mathematically combining related x-ray beam subpaths, but a volume slice having some depth. X-ray absorbency, measured as x-ray intensity by the detector elements, is a measure according to depth. Without measuring x-ray absorbency over a depth, there would be little or no contrast between object regions of different density. Thus, a reconstructed image array represents a two dimensional object plane within a reconstructed "slice". A slice is a substantially planar region within the object having some depth. The term "voxel" refers to a volume element located within a slice of the object to be imaged.

The image reconstruction method of the present invention generates information for a wide variety of planes and slices at numerous positions between the source and detector planes. The ability to reconstruct a wide variety of planes/slices is used to generate images of particular areas of the object by selecting a suitable slice near the region of interest of the object, without having to change the respective positions of the source and detector.

The image reconstruction method also increases the effective depth of field of a generated image by providing the capability to reconstruct multiple planes/slices in a region of interest. The image planes, which represent reconstructed slices, can be combined to produce a single array of image pixels with high spatial resolution in the area of interest.

Figure 6:
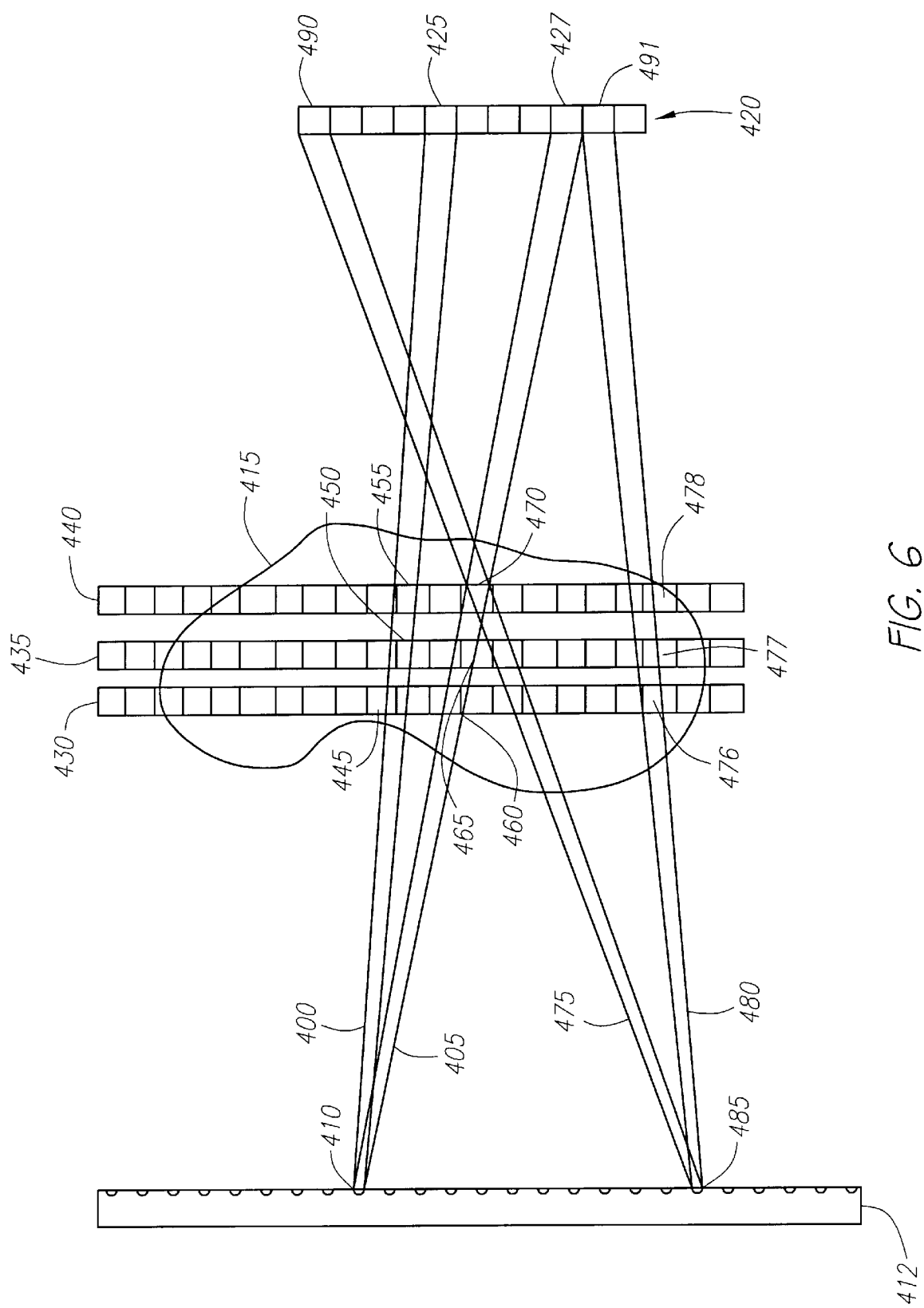
FIG. 6 is a diagram illustrating x-ray beam subpaths through an object to a detector array.

Referring to FIG. 6, a first x-ray beam subpath 400 and second x-ray beam subpath 405 are two of many x-ray beam subpaths emanating from a first aperture 410 of collimation grid 412. The remaining x-ray beam subpaths are not shown for the sake of clarity and explanation. Some of the x-rays that travel along first x-ray beam subpath 400 and second x-ray beam subpath 405 pass through object 415 and strike detectors 425 and 427, respectively, of multi-detector array 420. The information provided to detector 425 by x-rays traveling along first x-ray beam subpath 400 does not correspond to any single point within object 415, rather the path of the first x-ray beam subpath 400 as it passes through the object 415 forms a volume which intersects first slice 430, second slice 435, and third slice 440. Particularly, x-rays traveling along first x-ray beam subpath 400 creates a volume which is completely or partially coincident with first voxel 445, second voxel 450, and third voxel 455. For the purposes of reconstruction, the information obtained by detector 425 from x-ray beam subpath 400 can be used to generate an image pixel representing first voxel 445 in an image plane representing slice 430, can be used to generate an image pixel representing second voxel 450 in an image plane representing slice 435, and/or can be used to generate an image pixel representing third voxel 455 in an image plane representing slice 440. From this data, image planes are created using the methods described with respect to FIGS. 2–6.

With respect to second x-ray beam subpath 405, the information provided by detector 427 can be used to generate an image pixel representing fourth voxel 460 in an image plane representing slice 430, can be used to generate an image pixel representing fifth voxel 465 in an image plane representing slice 435, and/or can be used to generate an image pixel representing sixth voxel 470 in an image plane representing slice 440.

A third x-ray beam subpath 475 and fourth x-ray beam subpath 480 are two of many x-ray beam subpaths emanating from a second aperture 485. The remaining x-ray beam subpaths emanating from second aperture 485 are not shown for the sake of clarity and explanation. Some of the x-rays that travel along x-ray beam subpath 475 and x-ray beam subpath 480 pass through object 415 and strike detectors 490 and 491, respectively. The intensity information provided to detector 490 by x-rays traveling along third x-ray beam subpath 480 does not correspond to any single point within object 415, rather the intensity information is an aggregation of information for a volume that insects all plane/slices between collimation grid 412 and multi-detector array 420, including the planes/slices containing voxels 476, 477, and 478.

In an embodiment, an image pixel is created by combining or summing the intensity for a voxel from all of the detectors that detect x-rays traveling along x-ray beam subpaths that are completely or partially coincident with that particular voxel and have been assigned to that voxel for the purpose of reconstruction. For example, an image pixel representing sixth voxel 470 would include intensity data collected by detector 427 from x-ray beam subpaths 405 and intensity data collected by detector 490 from x-ray beam subpath 475.

The preferred reconstruction method individually reconstructs a number of slices simultaneously. In the example of FIG. 6, slices 430, 435 and 440 are reconstructed individually, and the various image pixels/voxels that make up each slice are combined or otherwise manipulated to create an array of display pixels for producing an image on a display monitor or film.

The image pixels of the reconstructed slices, can be stored in a memory as image planes, and can be used to display an image on a two dimensional display. A two dimensional display is composed of the array of display pixels that each represent a position on the display. The display pixels have only two dimensions, x and y, whereas the image pixels have not only x and y coordinates but also a z coordinate corresponding to the distance of the image pixel from the source (or detector). For example, the image pixels in the slice closest to the source can be assigned a z value of 1 and the image pixels in the image slice farthest from the source can be assigned a z value of p, where p is the total number of image slices created.

If an image on a two dimensional display is created by combining all the image planes together, the display pixels may appear as an image with indistinct edges. This is because the image displayed may not correspond to only one or two image pixels but to all of the image pixels that have the same x and y coordinates on differing image planes. In order to view meaningful images, preferably only one image pixel out of a number of image pixels having a different z coordinates but having the same x and y coordinates is selected for display as a display pixel. Note that when using this invention, the display image can focus upon more than one region or structure of interest at multiple depths and multiple x,y coordinates within an object that is being imaged.

Alternatively, it is possible to form part of the display image by combining one or more image pixels having the same x and y coordinates from different image planes/slices. The combined intensity data for the image pixels having the same x and y coordinates but different z coordinates can be displayed as a single display pixel with the appropriate x-y coordinates. Combining image pixels from two or more planes/slices can be performed if relevant information about the object(s) under investigation is located on multiple image planes/slices, and if it is more appropriate to form a display pixel representing the multiple sets of information than it is to select only one of the image pixels for display.

There are a number of methods that can be used to select which of the image pixels that have the same x and y coordinates but different z coordinates corresponding to different image planes/slices to display. A currently preferred method for selection is a maximum intensity projection algorithm. For each set of image pixels which have the same x and y coordinates but a different z coordinate, the maximum x-ray intensity projection algorithm selects the image pixel that has the greatest intensity value from the set. This image pixel which has the maximum x-ray intensity or luminance value is then displayed on the display as a display pixel having the appropriate x and y coordinates.

An alternative algorithm is a minimum intensity projection algorithm that selects for display the image pixel of the set of image pixels having the same x and y coordinates but different z coordinates that has the lowest intensity or luminance value.

Another method for selecting which of the image pixels that have the same x and y coordinates but different z coordinates corresponding to different image planes/slices to display involves selection of a portion of a plane/slice which has the greatest contrast in a particular region in order to display an object in the field of view.

Another method for selecting which of the image pixels that have the same x and y coordinates but different z coordinates corresponding to different image planes/slices to display involves selection of a portion of a plane/slice which has the greatest energy within a particular spatial frequency range in a particular region in order to display an object in a field of view.

Yet another method for selecting which of the image pixel that have the same x and y coordinates but different z coordinates corresponding to different image planes/slices to display involves selection of a portion of a plane/slice which has the greatest detail in a particular region in order to display an object in the field of view. In an embodiment of this approach, for each image pixel ($I_{x,y}$) two of the nearest neighbors are used to determine the slope as follows:

$$Slope = \sqrt{(I_{x,y} - I_{x+1,y})^2 + (I_{x,y} - I_{x,y+1})^2} \qquad EQ. 5$$

An alternate slope or gradient determination can be performed in which the absolute value of the difference of adjacent or otherwise neighboring pixels are calculated to determine the slope. For example, the following equation can be used to determine the slope:

$$Slope = |I_{x,y} - I_{x+1,y}| + |I_{x,y} - I_{x,y+1}| \qquad EQ. 6$$

The image pixel ($I_{x,y}$) that has the largest slope of the group having the same x,y but different z coordinates is then chosen for display. Other slope calculations may be utilized within the scope of the invention, including taking into account image pixels within the same vicinity or other methods of calculating, including weighting the image pixel slope values depending on the positioning of the image pixels.

In an alternative embodiment, it is possible that a display is created by selecting all of the image pixels from a single image plane for display. In an embodiment, the single plane selected is the one which has the greatest contrast within the plane as a whole.

It is further possible to combine any two or more of the disclosed methods depending upon the needs of the particular use or application.

Note that the foregoing methods for selecting which of the image pixels that have the same x and y coordinates but different z coordinates corresponding to different image planes/slices to display can be equally applied to other imaging modalities that reconstruct planes/slices (or other types of imaging data) at various depths within an object. For example, the methods can be applied to multi-slice CT data to display an image of an object in the field of view.

While the embodiments, applications and advantages of the present invention have been depicted and described, there are many more embodiments, applications and advantages possible without deviating from the spirit of the inventive concepts described herein. The invention should therefore only be restricted in accordance with the spirit of the claims appended hereto and is not restricted by the preferred embodiments, specification or drawings.

What is claimed is:

1. A method for generating an image comprising:
   generating x-rays from an x-ray source;
   passing the x-rays through an object to be imaged;
   detecting the x-rays with an x-ray detector;
   forming a volume of data about the object from detected x-rays, the volume of data comprising information from a plurality of depths within the object;
   selecting particular data from the volume of data to generate a display image based upon information from said volume of data pertaining to one or more structures within the object, wherein the act of selecting particular data from said volume of data is not based upon a planar relationship of the selected data.

2. The method of claim 1 in which the x-ray detector comprises an array of detector elements.

3. The method of claim 1 in which the volume of data comprises a plurality of image planes.

4. The method of claim 3 in which the image planes comprise an array of image pixels.

5. The method of claim 1 in which the volume of data comprises a plurality of image slices.

6. The method of claim 5 in which the image slices comprise a plurality of voxels.

7. The method of claim 1 in which the act of selecting particular data from the volume of data is based upon the intensity value of selected data.

8. The method of claim 7 in which the selected data is selected for maximum intensity.

9. The method of claim 7 in which the selected data is selected for minimum intensity.

10. The method of claim 1 in which the act of selecting particular data from the volume of data is based upon the relative contrast of selected data.

11. A method for generating an image comprising:
    generating x-rays from an x-ray source;
    passing the x-rays through an object to be imaged;
    detecting the x-rays with an x-ray detector;
    forming a volume of data about the object from detected x-rays, the volume of data comprising information from a plurality of depths within the object;
    selecting particular data from the volume of data to generate a display image that focuses upon one or more structures within the object, wherein the act of selecting particular data from the volume of data is based upon the level of detail within selected data.

12. A method for generating an image comprising:
generating x-rays from an x-ray source;
passing the x-rays through an object to be imaged;
detecting the x-rays with an x-ray detector;
forming a volume of data about the object from detected x-rays, the volume of data comprising information from a plurality of depths within the object;
selecting particular data from the volume of data to generate a display image that focuses upon one or more structures within the object, wherein the act of selecting particular data from the volume of data is based upon the energy within a particular spatial frequency range for selected data.

13. The method of claim 1 in which the volume of data is formed by a computed tomography imaging system.

14. The method of claim 1 in which the volume of data is formed by a reverse-geometry x-ray imaging system.

15. A method for generating an image comprising:
generating x-rays from an x-ray source;
passing the x-rays through an object to be imaged;
detecting the x-rays with an x-ray detector;
forming data about the object from detected x-rays, the data comprising information from a plurality of depths within the object;
selecting a set of the data corresponding to a plurality of depths within the object to generate a display image, wherein the act of selecting a set of the data is not based upon a planar relationship of the selected set of the data.

16. The method of claim 15 in which the x-ray detector comprises an array of detector elements.

17. The method of claim 15 in which the data comprises a plurality of image planes.

18. The method of claim 17 in which each of the plurality of image planes comprises an array of image pixels.

19. The method of claim 15 in which the data comprises a plurality of image slices.

20. The method of claim 19 in which each of the plurality of image slices comprises a plurality of voxels.

21. The method of claim 15 in which the act of selecting a set of the data is based upon the intensity value of selected data.

22. The method of claim 21 in which the selected data is selected for maximum intensity.

23. The method of claim 21 in which the selected data is selected for minimum intensity.

24. The method of claim 15 in which the act of selecting a set of the data is based upon the relative contrast of selected data.

25. A method for generating an image comprising:
generating x-rays from an x-ray source;
passing the x-rays through an object to be imaged;
detecting the x-rays with an x-ray detector;
forming data about the object from detected x-rays, the data comprising information from a plurality of depths within the object;
selecting a set of the data corresponding to a plurality of depths within the object to generate a display image, wherein the act of selecting a set of the data is based upon the level of detail within selected data.

26. A method for generating an image comprising:
generating x-rays from an x-ray source;
passing the x-rays through an object to be imaged;
detecting the x-rays with an x-ray detector;
forming data about the object from detected x-rays, the data comprising information from a plurality of depths within the object;
selecting a set of the data corresponding to a plurality of depths within the object to generate a display image, wherein the act of selecting a set of data is based upon the energy within a particular spatial frequency range for selected data.

27. The method of claim 15 in which the data is formed by a computed tomography imaging system.

28. The method of claim 15 in which the data is formed by a reverse-geometry x-ray imaging system.

29. A method for generating an image comprising:
forming data about an object to be imaged, the data comprising information from a plurality of depths within the object;
selecting a set of data from the data corresponding to a plurality of depths within the object to be imaged; and
generating a display image from the set of data that have been selected, wherein the act of selecting a set of data from the data is not based upon a planar relationship of the selected set of data.

30. The method of claim 29 in which the act of forming data comprises the use of an x-ray imaging system.

31. The method of claim 30 in which the x-ray imaging system comprises a reverse-geometry x-ray imaging system.

32. The method of claim 30 in which the x-ray imaging system comprises a computed tomography imaging system.

33. The method of claim 29 in which the act of selecting a set of the data is based upon the intensity value of selected data.

34. The method of claim 33 in which the selected data is selected for maximum intensity.

35. The method of claim 33 in which the selected data is selected for minimum intensity.

36. The method of claim 29 in which the act of selecting a set of the data is based upon the relative contrast of selected data.

37. A method for generating an image comprising:
forming data about an object to be imaged, the data comprising information from a plurality of depths within the object;
selecting a set of data from the data corresponding to a plurality of depths within the object to be imaged; and
generating a display image from the set of data that have been selected, wherein the act of selecting a set of the data is based upon the level of detail within selected data.

38. A method for generating an image comprising:
forming data about an object to be imaged, the data comprising information from a plurality of depths within the object;
selecting a set of data from the data corresponding to a plurality of depths within the object to be imaged; and
generating a display image from the set of data that have been selected, wherein the act of selecting a set of the data is based upon the energy within a particular spatial frequency range for selected data.

* * * * *